(12) United States Patent
Matulic-Adamic et al.

(10) Patent No.: US 6,489,465 B2
(45) Date of Patent: Dec. 3, 2002

(54) XYLOFURANOSLY-CONTAINING NUCLEOSIDE PHOSPHORAMIDITES AND POLYNUCLEOTIDES

(75) Inventors: Jasenka Matulic-Adamic, Boulder, CO (US); Leonid Beigelman, Longmont, CO (US)

(73) Assignee: Ribozyme Pharmaceuticals, Inc., Boulder, CO (US)

(*) Notice: Subject to any disclaimer, the term of this patent is extended or adjusted under 35 U.S.C. 154(b) by 0 days.

(21) Appl. No.: 09/960,192

(22) Filed: Sep. 21, 2001

(65) Prior Publication Data

US 2002/0028919 A1 Mar. 7, 2002

Related U.S. Application Data

(63) Continuation of application No. 09/135,964, filed on Aug. 18, 1998, now Pat. No. 6,316,612.
(60) Provisional application No. 60/056,808, filed on Aug. 22, 1997.

(51) Int. Cl.[7] .................. C07H 21/00; C07H 21/02; C07H 21/04; C12Q 1/68; A01N 61/00
(52) U.S. Cl. ............... 536/24.5; 536/22.1; 536/23.1; 536/25.3; 435/6; 514/1; 514/44
(58) Field of Search .................. 536/22.1, 23.1, 536/24.5, 25.3; 514/1, 44; 435/6

(56) References Cited

U.S. PATENT DOCUMENTS

| | | | |
|---|---|---|---|
| 4,987,071 A | 1/1991 | Cech et al. | 435/91 |
| 5,334,711 A | 8/1994 | Sproat et al. | 536/24.5 |
| 5,489,677 A | 2/1996 | Sanghvi | 536/22.1 |
| 5,616,459 A | 4/1997 | Kramer et al. | 435/5 |
| 5,625,047 A | 4/1997 | Been et al. | 536/23.1 |
| 5,631,359 A | 5/1997 | Chowrira et al. | 536/24.5 |
| 5,635,385 A | 6/1997 | Leopold et al. | 435/6 |
| 6,316,612 B1 * | 11/2001 | Matulic-Adamic et al. | 536/24.5 |

FOREIGN PATENT DOCUMENTS

| | | |
|---|---|---|
| EP | 0 360 257 A2 | 3/1990 |
| WO | 91/03162 | 3/1991 |
| WO | 92/07065 | 4/1992 |
| WO | 93/15187 | 5/1993 |
| WO | 93/23569 | 11/1993 |
| WO | 94/02595 | 2/1994 |
| WO | 95/13378 | 5/1995 |
| WO | 95/23225 | 8/1995 |
| WO | 96/10390 | 4/1996 |
| WO | 96/10391 | 4/1996 |
| WO | 96/10392 | 4/1996 |
| WO | 96/18736 | 6/1996 |
| WO | 96/19577 | 6/1996 |
| WO | 98/32880 | 7/1998 |

OTHER PUBLICATIONS

Grasby et al., "Applications of Synthetic Oligoribonucleotide Analogues in Studies of RNA Structure and Function," *Proc. Indian Acad. Sci.* 106(5):1003–1022 (1994).

Guerrier–Takada et al., "The RNA Moiety of Ribonuclease P Is the Catalytic Subunit of the Enzyme," *Cell* 35:849–857 (1983).

Guo and Collins, "Efficient trans–cleavage of a stem–loop RNA substrate by a ribozyme derived from Neurospora VS RNA," *EMBO J.* 14:368–376 (1995).

Hall, *The Modified Nucleosides in Nucleic Acids,* Columbia University Press (1971) (Table of Contents Only).

Hampel and Tritz, "RNA Catalytic Properties of the Minimum (–)sTRSV Sequence," *Biochemistry* 28:4929–4933 (1989).

(List continued on next page.)

*Primary Examiner*—Jezia Riley
(74) *Attorney, Agent, or Firm*—McDonnell Boehnen Hulbert & Berghoff

(57) ABSTRACT

Novel xylo nucleoside or xylo nucleotide analogs, polynucleotides comprising xylo nucleotide substitution, processes for their synthesis and incorporation into polynucleotides.

20 Claims, 4 Drawing Sheets

OTHER PUBLICATIONS

Hampel et al., "'Hairpin' Catalytic RNA Model: Evidence for Helices and Sequence Requirement for Substrate RNA," *Nucleic Acids Research* 18:299–304 (1990).

Haseloff and Gerlach, "Simple RNA Enzymes with New and Highly Specific Endoribonuclease Activities," *Nature* 334:585–591 (1988).

Hutchinson et al., "Ch.3—The Synthesis, Reactions and Properties of Nucleoside Mono–, Di–, Tri–, and Tetraphosphates and Nucleotides with Changes in the Phosphoryl Residue," *Chemistry of Nucleosides and Nucleotides, vol. 2*, edited by L.B. Townsend, Plenum Press, New York, pp. 81–160 (1991).

Ishiwata et al., "Physical–Chemistry Characteristics and Biodistribution of Poly(ethylene glycol)–Coated Liposomes Using Poly(oxyethylene) Cholesteryl Ether," *Chem. Pharm. Bull.* 43:1005–1011 (1995).

Jarvis et al., "Inhibition of Vascular Smooth Muscle Cell Proliferation by Hammerhead Ribozymes Targeting C–Myb," Journal of Cellular Biochemistry 19A:221 (1995) (Abstract only XP 002024063).

Jeffries and Symons, "A Catalytic 13–mer Ribozyme," *Nucleic Acids Research* 17:1371–1377 (1989).

Kim and Cech, "Three–dimensional model of the active site of the self–splicing rRNA precursor of Tetrahymena," *Proc. Natl. Acad. Sci. USA* 84:8788–8792 (1987).

Lasic and Needham "The 'Stealth' Liposome: A Prototypical Biomaterial," *Chemical Reviews* 95:2601–2627 (1995).

Lasic and Papahadjopoulos, "Liposomes Revisited," *Science* 267:1275–1276 (1995).

Limbach et al., "Summary: the modified nucleosides of RNA," *Nucleic Acids Research* 22(12):2183–2196 (1994).

Liu et al., "Cationic Liposome–mediated Intravenous Gene Delivery," *J. Biol. Chem.* 270(42):24864–24870 (1995).

Milligan and Uhlenbeck, "Synthesis of Small RNAs Using T7 RNA Polymerase," *Methods Enzymol.* 180:51–62 (1989).

Nathans and Smith, "Restriction Endonucleases in the Analysis and Restructuring of DNA Molecules," *Ann. Rev. Biochem.* 44:273–293 (1975).

Oku et al., "Real–time analysis of liposomal trafficking in tumor–bearing mice by use of positron emission tomography," *Biochimica et Biophysica Acta* 1238:86–90 (1995).

Pace and Smith, "Ribonuclease P: Function and Variation," *J. Biol. Chem.* 265:3587–3590 (1990).

Perreault et al., "Mixed Deoxyribo– and Ribo–Oligonucleotides with Catalytic Activity," *Nature* 344:565–567 (1990).

Perrotta and Been, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Pyle et al., "Building a Kinetic Framework for Group II Intron Ribozyme Activity: Quantitation of Interdomain Binding and Reaction Rate," *Biochemistry* 33:2716–2725 (1994).

Rosemeyer and Seela, "72. 1(2'Deoxy–β–D–xylofuranosyl) thymine Building Blocks for Solid–Phase Synthesis and Properties of Oligo (2–Deoxyxylonucleotides)," *Helvetica Chimica Acta* 74:748–760 (1991).

Rossi and Sarver, "RNA enzymes (ribozymes) as antiviral therapeutic agents," *TIBTECH* 8:179–183 (1990).

Saville and Collins, "A Site–Specific Self–Cleavage Reaction Performed by a Novel RNA In *Neurospora mitochondria*," *Cell* 61:685–696 (1990).

Saville and Collins, "RNA–Mediated Ligation of SelfCleavage Products of a *Neurospora mitochondrial* Plasmid Transcript," *Proc. Natl. Acad. Sci. USA* 88:8826–8830 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Seela et al., "83. 1(2'–Deoxy–β–D–xylofuranosyl)cytosine: Base Pairing of Oligonucleotides with a Configurationally Altered Sugar–Phosphate Backbone," *Helvetica Chimica Acta* 77:883–896 (1994).

Seela et al., "122. Xylose–DNA Containing the Four Natural Bases," *Helvetica Chimica Acta* 79:1451–1461 (1996).

Stein and Cheng, "Antisense Oligonucleotides as Therapeutic Agents—Is the Bullet Really Magical?" *Science* 261:1004–1288 (1993).

Torrence et al., "Targeting RNA for degradation with a (2'–5') oligoadenylate–antisense chimera," *Proc. Natl. Acad. Sci. USA* 90:1300–1304 (1993).

Tuschl et al., "Importance of Exocyclic Base Functional Groups of Central Core Guansoines for Hammerhead Ribozyme Activity," *Biochemistry* 32:11658–11668 (1993).

Uhlmann and Peyman, "Antisense Oligonucleotides: A New Therapeutic Principle," *Chemical Reviews* 90:544–584 (1990).

Usman and Cedergren, "Exploiting the chemical synthesis of RNA," *TIBS* 17:334–339 (1992).

Usman and McSwiggen, "Ch. 30—Catalytic RNA (Ribozymes) as Drugs," *Annual Reports in Medicinal Chemistry* 30:285–294 (1995).

Usman et al., "Automated Chemical Synthesis of Long Oligoribonucleotides Using 2'–O–Silyated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Usman et al., "Chemical modification of hammerhead ribozymes: activity and nuclease resistance," *Nucleic Acids Syposium Series* 31:163–164 (1994).

Usman et al., "Hamerhead ribozyme engineering," *Current Opinion in Structural Biology* 1:527–533 (1996).

Wincott et al., "Synthesis, deprotection, analysis and purification of RNA and ribozymes," *Nucleic Acids Research* 23(14):2677–2684 (1995).

Zaug et al., "The Tetrahymena Ribozyme Acts Like and RNA Restriction Endonuclease," *Nature* 324:429–433 (1986).

* cited by examiner

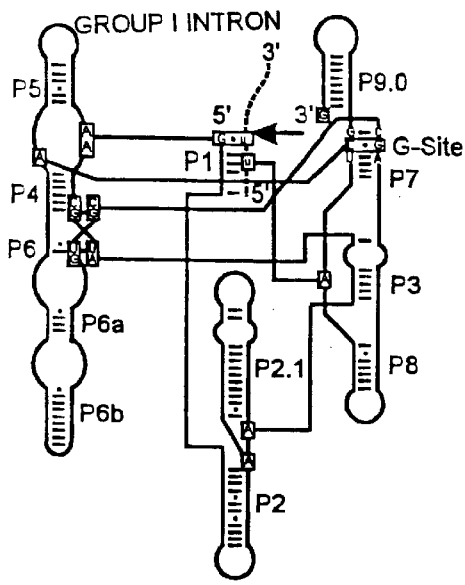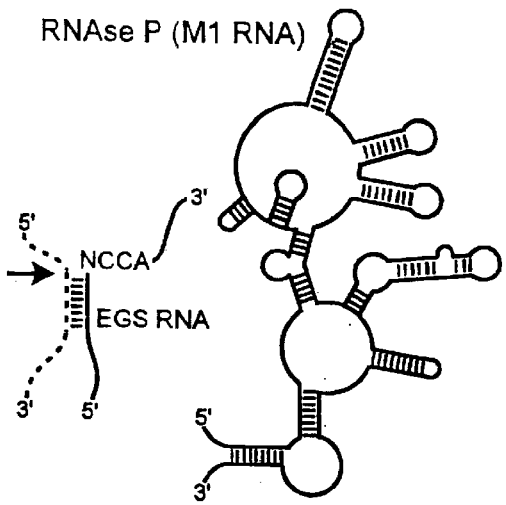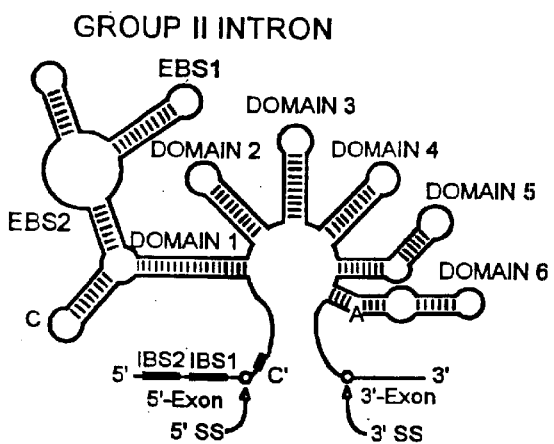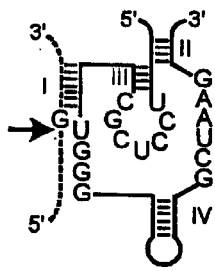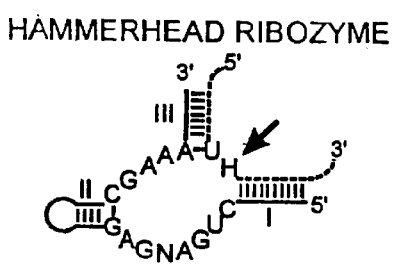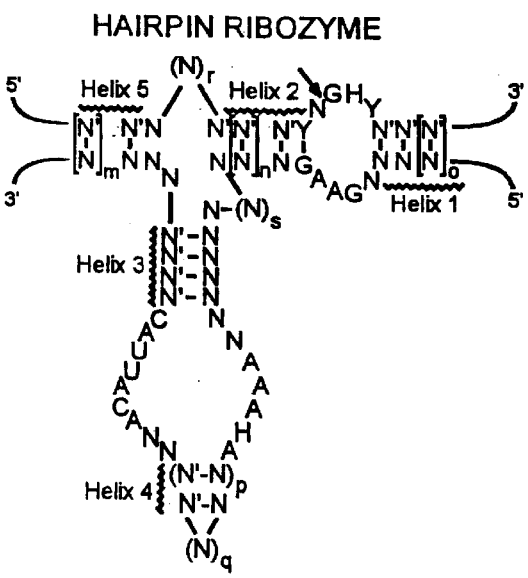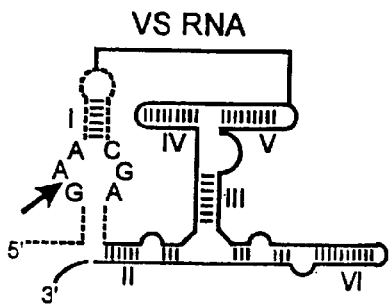
Fig. 1

Figure 2: Synthesis of a Xylo ribonucleoside phosphoramidite
Scheme 1
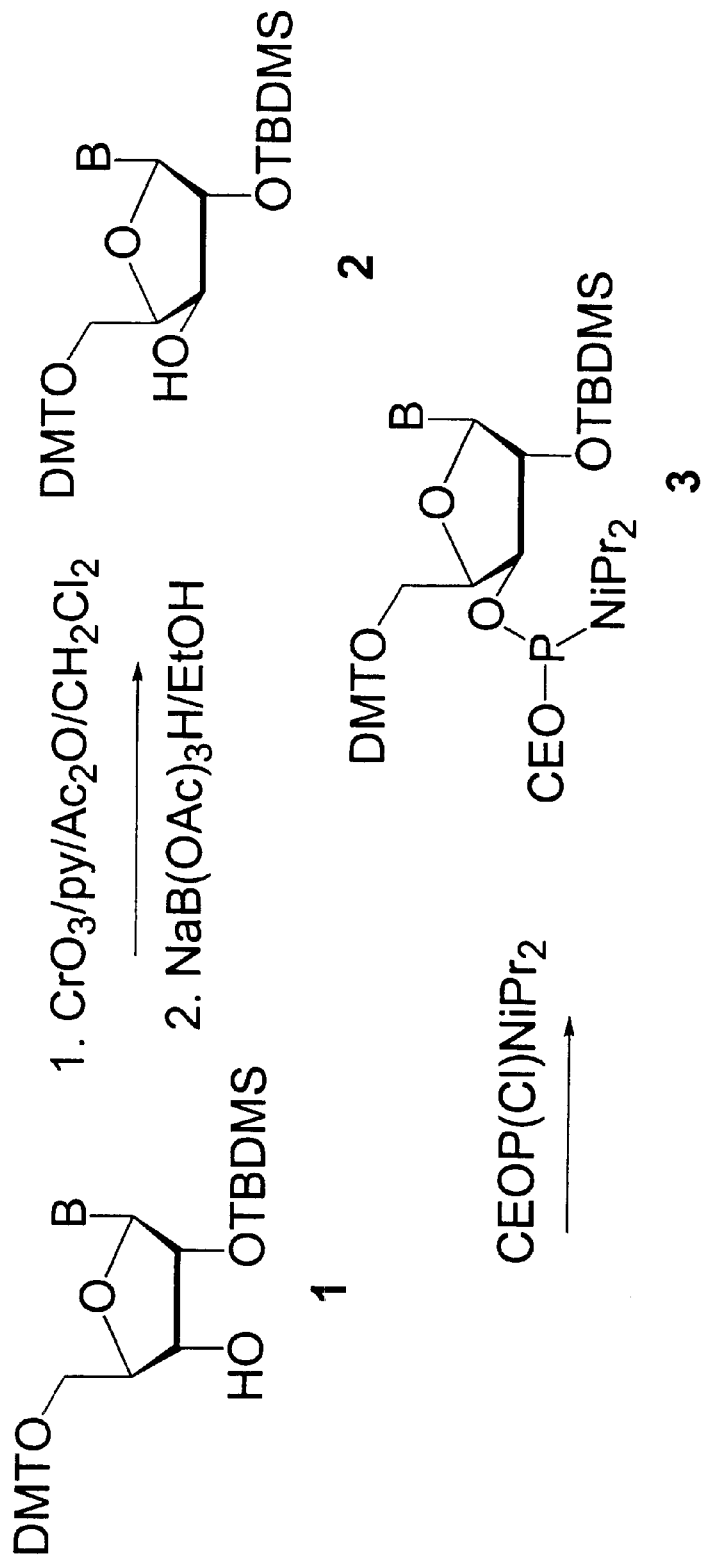
B = standard or modified nucleotide base or H

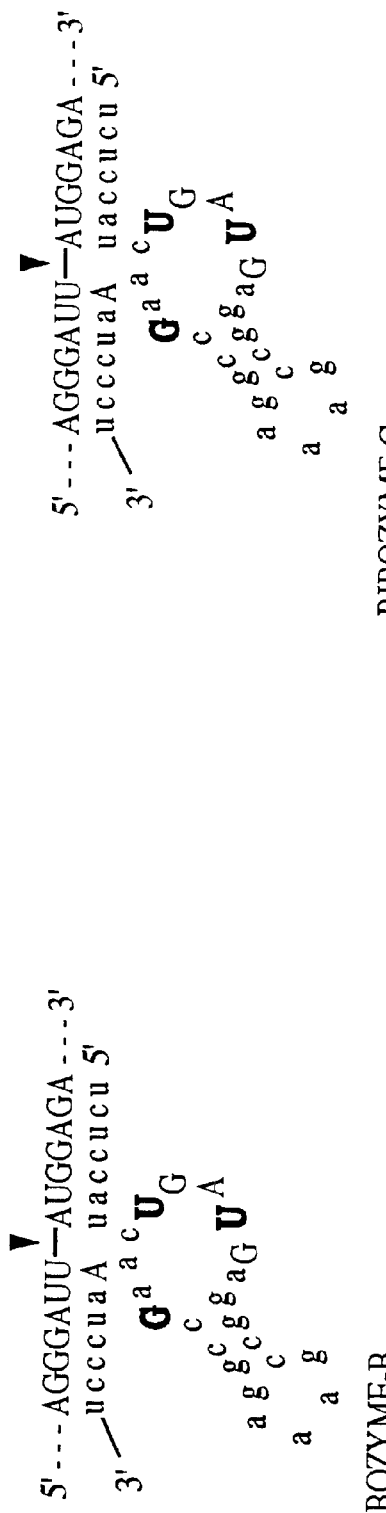
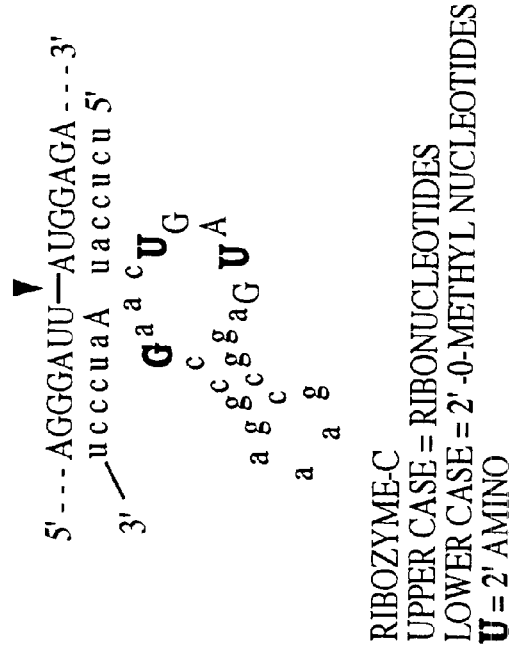
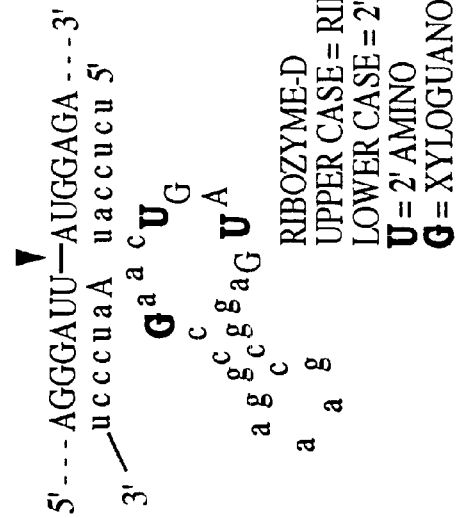
FIG. 3A

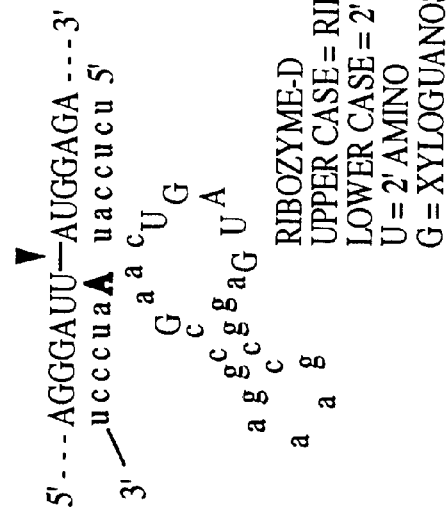
FIG. 3B

XYLOFURANOSLY-CONTAINING NUCLEOSIDE PHOSPHORAMIDITES AND POLYNUCLEOTIDES

CROSS-REFERENCE TO RELATED APPLICATIONS

This is a continuation of application Ser. No. 09/135,964 filed on Aug. 18, 1998 now U.S. Pat. No. 6,316,612 which claims the benefit of Ser. No. 60/056,808, filed on Aug. 22, 1997.

BACKGROUND OF THE INVENTION

This invention relates to novel nucleoside or nucleotide analogs, and processes for their synthesis and incorporation into polynucleotides.

The following is a brief description of nucleoside analogs. This summary is not meant to be complete but is provided only for an understanding of the invention that follows. This summary is not an admission that all of the work described below is prior art to the claimed invention.

Nucleoside modifications of bases and sugars, have been discovered in a variety of naturally occurring RNA (e.g., tRNA, mRNA, rRNA; reviewed by Hall, 1971 *The Modified Nucleosides in Nucleic Acids,* Columbia University Press, New York; Limbach et al., 1994 *Nucleic Acids Res.* 22, 2183). In an attempt to understand the biological significance, structural and thermodynamic properties, and nuclease resistance of these nucleoside modifications in nucleic acids, several investigators have chemically synthesized nucleosides, nucleotides and phosphoramidites with various base and sugar modifications and incorporated them into oligonucleotides.

Uhlmann and Peyman, 1990, *Chem. Reviews* 90, 543, review the use of certain nucleoside modifications to stabilize antisense oligonucleotides.

Usman et al., International PCT Publication Nos. WO/93/15187; and WO 95/13378; describe the use of sugar, base and backbone modifications to enhance the nuclease stability of enzymatic nucleic acid molecules.

Eckstein et al., International PCT Publication No. WO 92/07065 describe the use of sugar, base and backbone modifications to enhance the nuclease stability of enzymatic nucleic acid molecules.

Grasby et al., 1994, *Proc. Indian Acad. Sci.,* 106, 1003, review the "applications of synthetic oligoribonucleotide analogues in studies of RNA structure and function".

Eaton and Pieken, 1995, *Annu. Rev. Biochem.,* 64, 837, review sugar, base and backbone modifications that enhance the nuclease stability of RNA molecules.

Rosemeyer et al., 1991, *Helvetica Chem. Acta,* 74, 748, describe the synthesis of 1-(2'-deoxy-β-D-xylofuranosyl) thymine-containing oligodeoxynucleotides.

Seela et al., 1994, *Helvetica Chem. Acta,* 77, 883, describe the synthesis of 1-(2'-deoxy-β-D-xylofuranosyl) cytosine-containing oligodeoxynucleotides.

Seela et al., 1996, *Helvetica Chem. Acta,* 79, 1451, describe the synthesis xylose-DNA containing the four natural bases.

The references cited above are distinct from the presently claimed invention since they do not disclose and/or contemplate the synthesis of xylofuranosyl nucleoside phosphoamidites and polynucleotides comprising such nucleotide modifications of the instant invention.

SUMMARY OF THE INVENTION

This invention relates to a compound having the Formula I:

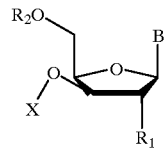

wherein, $R_1$ is OH, O—$R_3$, where $R_3$ is independently a moiety selected from a group consisting of alkyl, alkenyl, alkynyl, aryl, alkylaryl, carbocyclic aryl, heterocyclic aryl, amide and ester; C—$R_3$, where $R_3$ is independently a moiety selected from a group consisting of alkyl, alkenyl, alkynyl, aryl, alkylaryl, carbocyclic aryl, heterocyclic aryl, amide and ester; halo, $NHR_4$ ($R_4$=alkyl (C1–22), acyl (C1–22), substituted or unsubstituted aryl), or $OCH_2SCH_3$ (methylthiomethyl), $ONHR_5$ where $R_5$ is independently H, aminoacyl group, peptidyl group, biotinyl group, cholesteryl group, lipoic acid residue, retinoic acid residue, folic acid residue, ascorbic acid residue, nicotinic acid residue, 6-aminopenicillanic acid residue, 7-aminocephalosporanic acid residue, alkyl, alkenyl, alkynyl, aryl, alkylaryl, carbocyclic aryl, heterocyclic aryl, amide or ester, ON=$R_6$, where $R_6$ is independently pyridoxal residue, pyridoxal-5-phosphate residue, 13-cis-retinal residue, 9-cis-retinal residue, alkyl, alkenyl, alkynyl, alkylaryl, carbocyclic alkylaryl, or heterocyclic alkylaryl; B is independently a nucleotide base or its analog or hydrogen; X is independently a phosphorus-containing group; and $R_2$ is independently blocking group or a phosphorus-containing group.

Specifically, an "alkyl" group refers to a saturated aliphatic hydrocarbon, including straight-chain, branched-chain, and cyclic alkyl groups. Preferably, the alkyl group has 1 to 12 carbons. More preferably it is a lower alkyl of from 1 to 7 carbons, more preferably 1 to 4 carbons. The alkyl group may be substituted or unsubstituted. When substituted the substituted group(s) is preferably, hydroxy, cyano, alkoxy, $NO_2$ or $N(CH_3)_2$, amino, or SH.

The term "alkenyl" group refers to unsaturated hydrocarbon groups containing at least one carbon-carbon double bond, including straight-chain, branched-chain, and cyclic groups. Preferably, the alkenyl group has 1 to 12 carbons. More preferably it is a lower alkenyl of from 1 to 7 carbons, more preferably 1 to 4 carbons. The alkenyl group may be substituted or unsubstituted. When substituted the substituted group(s) is preferably, hydroxyl, cyano, alkoxy, $NO_2$, halogen, $N(CH_3)_2$, amino, or SH.

The term "alkynyl" refers to an unsaturated hydrocarbon group containing at least one carbon-carbon triple bond, including straight-chain, branched-chain, and cyclic groups. Preferably, the alkynyl group has 1 to 12 carbons. More preferably it is a lower alkynyl of from 1 to 7 carbons, more preferably 1 to 4 carbons. The alkynyl group may be substituted or unsubstituted. When substituted the substituted group(s) is preferably, hydroxyl, cyano, alkoxy, =O, =S, $NO_2$ or $N(CH_3)_2$, amino or SH.

An "aryl" group refers to an aromatic group which has at least one ring having a conjugated π electron system and includes carbocyclic aryl, heterocyclic aryl and biaryl groups, all of which may be optionally substituted. The preferred substituent(s) on aryl groups are halogen, trihalomethyl, hydroxyl, SH, cyano, alkoxy, alkyl, alkenyl, alkynyl, and amino groups.

An "alkylaryl" group refers to an alkyl group (as described above) covalently joined to an aryl group (as described above).

"Carbocyclic aryl" groups are groups wherein the ring atoms on the aromatic ring are all carbon atoms. The carbon atoms are optionally substituted.

"Heterocyclic aryl" groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, pyrrolo, pyrimidyl, pyrazinyl, imidazolyl and the like, all optionally substituted.

An "amide" refers to an —C(O)—NH—R, where R is either alkyl, aryl, alkylaryl or hydrogen.

An "ester" refers to an —C(O)—OR', where R is either alkyl, aryl, or alkylaryl.

A "blocking group" is a group which is able to be removed after polynucleotide synthesis and/or which is compatible with solid phase polynucleotide synthesis.

A "phosphorus containing group" can include phosphorus in forms such as dithioates, phosphoramidites and/or as part of an oligonucleotide.

In a preferred embodiment, the invention features a process for synthesis of the compounds of formula I.

In a preferred embodiment the invention features a process for the synthesis of a xylofuranosyl nucleoside phosphoramidite comprising the steps of: a) oxidation of a 2' and 5'-protected ribonucleoside with a an oxidant such as chromium oxide/pyridine/aceticanhydride, dimethylsulfoxide/aceticanhydride, or Dess-Martin reagent (periodinane) followed by reduction with a reducing agent such as, triacetoxy sodium borohydride, sodium borohydride, or lithium borohydride, under conditions suitable for the formation of 2' and 5'-protected xylofuranosyl nucleoside; b) phosphitylation under conditions suitable for the formation of xylofuranosyl nucleoside phosphoramidite.

In yet another preferred embodiment, the invention features the incorporation of the compounds of Formula I into polynucleotides. These compounds can be incorporated into polynucleotides enzymatically. For example by using bacteriophage T7 RNA polymerase, these novel nucleotide analogs can be incorporated into RNA at one or more positions (Milligan et al., 1989, *Methods Enzymol*, 180, 51). Alternatively, novel nucleoside analogs can be incorporated into polynucleotides using solid phase synthesis (Brown and Brown, 1991, in *Oligonucleotides and Analogues: A Practical Approach*, p. 1, ed. F. Eckstein, Oxford University Press, New York; Wincott et al., 1995, *Nucleic Acids Res.*, 23, 2677; Beaucage & Caruthers, 1996, in *Bioorganic Chemistry: Nucleic Acids*, p 36, ed. S. M. Hecht, Oxford University Press, New York).

The compounds of Formula I can be used for chemical synthesis of nucleotide-tri-phosphates and/or phosphoramidites as building blocks for selective incorporation into oligonucleotides. These oligonucleotides can be used as an antisense molecule, 2-5A antisense chimera, triplex forming oligonucleotides (TFO) or as an enzymatic nucleic acid molecule. The oligonucleotides can also be used as probes or primers for synthesis and/or sequencing of RNA or DNA.

The compounds of the instant invention can be readily converted into nucleotide diphosphate and nucleotide triphosphates using standard protocols (for a review see Hutchinson, 1991, in *Chemistry of Nucleosides and Nucleotides*, v.2, pp 81–160, Ed. L. B. Townsend, Plenum Press, New York, USA; incorporated by reference herein).

The compounds of Formula I can also be independently or in combination used as an antiviral, anticancer or an antitumor agent. These compounds can also be independently or in combination used with other antiviral, anticancer or an antitumor agents.

By "antisense" it is meant a non-enzymatic nucleic acid molecule that binds to target RNA by means of RNA-RNA or RNA-DNA or RNA-PNA (protein nucleic acid; Egholm et al., 1993 *Nature* 365, 566) interactions and alters the activity of the target RNA (for a review see Stein and Cheng, 1993 *Science* 261, 1004).

By "2-5A antisense chimera" it is meant, an antisense oligonucleotide containing a 5' phosphorylated 2'-5'-linked adenylate residues. These chimeras bind to target RNA in a sequence-specific manner and activate a cellular 2-5A-dependent ribonuclease which, in turn, cleaves the target RNA (Torrence et al., 1993 *Proc. Natl. Acad. Sci. USA* 90, 1300).

By "triplex forming oligonucleotides (TFO)" it is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89, 504).

By "enzymatic nucleic acid" it is meant a nucleic acid molecule capable of catalyzing reactions including, but not limited to, site-specific cleavage and/or ligation of other nucleic acid molecules, cleavage of peptide and amide bonds, and trans-splicing. Such a molecule with endonuclease activity may have complementarity in a substrate binding region to a specified gene target, and also has an enzymatic activity that specifically cleaves RNA or DNA in that target. That is, the nucleic acid molecule with endonuclease activity is able to intramolecularly or intermolecularly cleave RNA or DNA and thereby inactivate a target RNA or DNA molecule. This complementarity functions to allow sufficient hybridization of the enzymatic RNA molecule to the target RNA or DNA to allow the cleavage to occur. 100% complementarity is preferred, but complementarity as low as 50–75% may also be useful in this invention. The nucleic acids may be modified at the base, sugar, and/or phosphate groups. The term enzymatic nucleic acid is used interchangeably with phrases such as ribozymes, catalytic RNA, enzymatic RNA, catalytic DNA, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The specific enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving activity to the molecule. The sites in such nucleic acid that can be modified with nucleotides described herein are known in the art, or standard methods can be used to determine useful such sites in other such nucleic acids. See, e.g., Usman, supra.

By "enzymatic portion" or "catalytic domain" is meant that portion/region of the ribozyme essential for cleavage of a nucleic acid substrate (for example see FIG. 7).

By "substrate binding arm" or "substrate binding domain" is meant that portion/region of a ribozyme which is complementary to (i.e., able to base-pair with) a portion of its substrate. Generally, such complementarity is 100%, but can be less if desired. For example, as few as 10 bases out of 14 may be base-paired. Such arms are shown generally in FIGS. 1 and 3. That is, these arms contain sequences within a ribozyme which are intended to bring ribozyme and target together through complementary base-pairing interactions. The ribozyme of the invention may have binding arms that are contiguous or non-contiguous and may be varying lengths. The length of the binding arm(s) are preferably greater than or equal to four nucleotides; specifically 12–100 nucleotides; more specifically 14–24 nucleotides long. If a ribozyme with two binding arms are chosen, then the length of the binding arms are symmetrical (i.e., each of the binding arms is of the same length; e.g., six and six nucleotides or seven and seven nucleotides long) or asymmetrical (i.e., the binding arms are of different length; e.g., six and three nucleotides or three and six nucleotides long).

In a preferred embodiment, a polynucleotide of the invention would bear one or more 2'-hydroxylamino functionalities attached directly to the monomeric unit or through the use of an appropriate spacer. Since oligonucleotides have neither aldehyde nor hydroxylamino groups, the formation of an oxime would occur selectively using an oligo as a polymeric template. This approach would facilitate the attachment of practically any molecule of interest (peptides, polyamines, coenzymes, oligosaccharides, lipids, etc.) directly to the oligonucleotide using either aldehyde or carboxylic function in the molecule of interest.

Scheme 1
Post synthetic Oxime Bond Formation

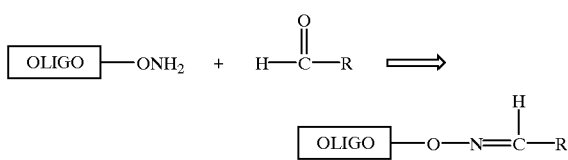

Scheme 2
Chemical Ligation of Oligonucleotides

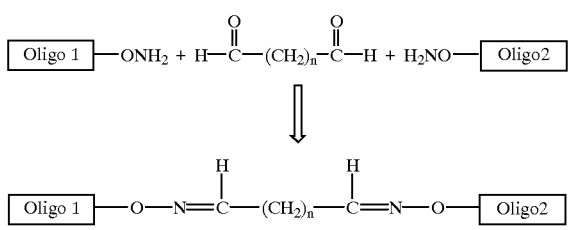

Advantages of oxime bond formation:

The oximation reaction proceeds in water

Quantitative yields

Hydrolytic stability in a wide pH range (5–8)

The amphoteric nature of oximes allows them to act either as weak acids or weak bases.

Oximes exhibit a great tendency to complex with metal ions

In yet another preferred embodiment, the aminooxy "tether" in oligonucleotides, such as a ribozyme, is reacted with different compounds bearing carboxylic groups (e.g. aminoacids, peptides, "cap" structures, etc.) resulting in the formation of oxyamides as shown below.

Scheme 3
Post synthetic oxyamide bond formation

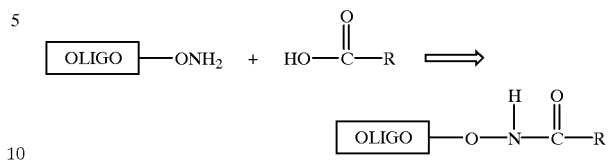

Other features and advantages of the invention will be apparent from the following description of the preferred embodiments thereof,, and from the claims.

DESCRIPTION OF THE PREFERRED EMBODIMENTS

The drawings will first briefly be described.

Drawings

FIG. 1 shows the secondary structure model for seven different classes of enzymatic nucleic acid molecules. Arrow indicates the site of cleavage. --------- indicate the target sequence. Lines interspersed with dots are meant to indicate tertiary interactions.—is meant to indicate base-paired interaction. Group I Intron: P1–P9.0 represent various stem-loop structures (Cech et al., 1994, *Nature Struc. Bio.*, 1, 273). RNase P (M1RNA): EGS represents external guide sequence (Forster et al., 1990, *Science*, 249, 783; Pace et al., 1990, *J. Biol. Chem.*, 265, 3587). Group II Intron: 5'SS means 5' splice site; 3'SS means 3'-splice site; IBS means intron binding site; EBS means exon binding site (Pyle et al., 1994, *Biochemistry*, 33, 2716). VS RNA: I–VI are meant to indicate six stem-loop structures; shaded regions are meant to indicate tertiary interaction (Collins, International PCT Publication No. WO 96/19577). HDV Ribozyme: : I–IV are meant to indicate four stem-loop structures (Been et al., U.S. Pat. No. 5,625,047). Hammerhead Ribozyme:: I–III are meant to indicate three stem-loop structures; stems I–III can be of any length and may be symmetrical or asymmetrical (Usman et al., 1996, *Curr. Op. Struct. Bio.*, 1, 527). Hairpin Ribozyme: Helix 1, 4 and 5 can be of any length; Helix 2 is between 3 and 8 base-pairs long; Y is a pyrimidine; Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is $\geq$1 base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is $\geq$2 bases. The connecting loop can also be replaced with a non-nucleotide linker molecule. H refers to bases A, U, or C. Y refers to pyrimidine bases.

"_" refers to a covalent bond. (Burke et al., 1996, *Nucleic Acids & Mol. Biol.*, 10, 129; Chowrira et al., U.S. Pat. No. 5,631,359).

FIG. 2 depicts a scheme for the synthesis of a xylo ribonucleoside phosphoramidite.

FIGS. 3A and 3B are a diagrammatic representation of hammerhead (HH) ribozyme targeted against stromelysin RNA (site 617) with various modifications.

Synthesis of Polynucleotides

Synthesis of polynucleotides greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure.

By "polynucleotide" as used herein is meant a molecule having two or more nucleotides. The polynucleotide can be single, double or multiple stranded and may comprise modified or unmodified nucleotides or non-nucleotides or various mixtures and combinations thereof.

RNA molecules, such as the ribozymes are chemically synthesized. The method of synthesis used follows the procedure for normal RNA synthesis as described in Usman et al., 1987 *J. Am. Chem. Soc.*, 109, 7845; Scaringe et al., 1990 *Nucleic Acids Res.*, 18, 5433; and Wincott et al., 1995 *Nucleic Acids Res.* 23, 2677–2684 and makes use of common nucleic acid protecting and coupling groups, such as dimethoxytrityl at the 5'-end, and phosphoramidites at the 3'-end. Small scale synthesis were conducted on a 394 Applied Biosystems, Inc. synthesizer using a modified 2.5 μmol scale protocol with a 5 min coupling step for alkylsilyl protected nucleotides and 2.5 min coupling step for 2'-O-methylated nucleotides. Table II outlines the amounts, and the contact times, of the reagents used in the synthesis cycle. A 6.5-fold excess (163 μL of 0.1 M=16.3 μmol) of phosphoramidite and a 24-fold excess of S-ethyl tetrazole (238 μL of 0.25 M=59.5 μmol) relative to polymer-bound 5'-hydroxyl was used in each coupling cycle. Average coupling yields on the 394 Applied Biosystems, Inc. synthesizer, determined by calorimetric quantitation of the trityl fractions, were 97.5–99%. Other oligonucleotide synthesis reagents for the 394 Applied Biosystems, Inc. synthesizer: detritylation solution was 2% TCA in methylene chloride (ABI); capping was performed with 16% N-methyl imidazole in THF (ABI) and 10% acetic anhydride/10% 2,6-lutidine in THF (ABI); oxidation solution was 16.9 mM $I_2$, 49 mM pyridine, 9% water in THF (Millipore). B & J Synthesis Grade acetonitrile was used directly from the reagent bottle. S-Ethyl tetrazole solution (0.25 M in acetonitrile) was made up from the solid obtained from American International Chemical, Inc.

Deprotection of the RNA was performed as follows. The polymer-bound oligoribonucleotide, trityl-off, was transferred from the synthesis column to a 4 mL glass screw top vial and suspended in a solution of methylamine (MA) at 65° C. for 10 min. After cooling to −20° C., the supernatant was removed from the polymer support. The support was washed three times with 1.0 mL of EtOH:MeCN:$H_2O$/3:1:1, vortexed and the supernatant was then added to the first supernatant. The combined supernatants, containing the oligoribonucleotide, were dried to a white powder.

The base-deprotected oligoribonucleotide was resuspended in anhydrous TEA.HF/NMP solution (250 μL of a solution of 1.5 mL N-methylpyrrolidinone, 750 μL TEA and 1.0 mL TEA•3HF to provide a 1.4M HF concentration) and heated to 65° C. for 1.5 h. The resulting, fully deprotected, oligomer was quenched with 50 mM TEAB (9 mL) prior to anion exchange desalting.

For anion exchange desalting of the deprotected oligomer, the TEAB solution was loaded onto a Qiagen 500® anion exchange cartridge (Qiagen Inc.) that was prewashed with 50 mM TEAB (10 mL). After washing the loaded cartridge with 50 mM TEAB (10 mL), the RNA was eluted with 2 M TEAB (10 mL) and dried down to a white powder.

RNAs are purified by gel electrophoresis using general methods or are purified by high pressure liquid chromatography (HPLC; See Stinchcomb et al., International PCT Publication No. WO 95/23225, the totality of which is hereby incorporated herein by reference) and are resuspended in water.

Enzymatic Nucleic Acid Molecules

The enzymatic nucleic acid is able to intramolecularly or intermolecularly cleave RNA or DNA and thereby inactivate a target RNA or DNA molecule. The enzymatic nucleic acid molecule that has complementarity in a substrate binding region to a specified gene target, also has an enzymatic activity that specifically cleaves RNA or DNA in that target. This complementarity functions to allow sufficient hybridization of the enzymatic RNA molecule to the target RNA or DNA to allow the cleavage to occur. 100% Complementarity is preferred, but complementarity as low as 50–75% may also be useful in this invention. The nucleic acids may be modified at the base, sugar, and/or phosphate groups.

The term enzymatic nucleic acid is used interchangeably with phrases such as ribozymes, catalytic RNA, enzymatic RNA, catalytic DNA, nucleozyme, DNAzyme, RNA enzyme, endoribonuclease, minizyme, leadzyme, oligozyme, or DNA enzyme.

By "complementarity" is meant a nucleic acid that can form hydrogen bond(s) with other RNA sequence by either traditional Watson-Crick or other non-traditional types (for example, Hoogsteen type) of base-paired interactions.

Nucleic acid molecules having an endonuclease enzymatic activity are able to repeatedly cleave other separate RNA molecules in a nucleotide base sequence-specific manner. Such enzymatic RNA molecules can be targeted to virtually any RNA transcript, and efficient cleavage achieved in vitro (Zaug et al., 324, *Nature* 429 1986; Kim et al., 84 *Proc. Natl. Acad. Sci. USA* 8788, 1987; Haseloff and Gerlach, 334 *Nature* 585, 1988; Cech, 260 *JAMA* 3030, 1988; and Jefferies et al., 17 *Nucleic Acids Research* 1371, 1989).

Because of their sequence-specificity, trans-cleaving ribozymes show promise as therapeutic agents for human disease (Usman & McSwiggen, 1995 *Ann. Rep. Med. Chem.* 30, 285–294; Christoffersen and Marr, 1995 J. Med. Chem. 38, 2023–2037). Ribozymes can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

Seven basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base-pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base-pairing. Thus, it is thought that the specificity of action of a ribozyme is greater than that of antisense oligonucleotide binding the same RNA site.

In one aspect, an enzymatic nucleic acid molecule is formed in a hammerhead (see for example FIGS. 1 and 2) or hairpin motif (FIG. 1), but may also be formed in the motif of a hepatitis delta virus (HDV), group I intron, RNaseP RNA (in association with an external guide sequence) or Neurospora VS RNA (FIG. 1). Examples of such hammerhead motifs are described by Rossi et al., 1992, *Aids Research and Human Retroviruses* 8, 183; Usman et al., 1996, *Curr. Op. Struct. Biol.,* 1, 527; of hairpin motifs by Hampel et al., EP 0360257; Hampel and Tritz, 1989 *Biochemistry* 28, 4929; and Hampel et al., 1990 *Nucleic Acids Res.* 18, 299; Chowrira et al., U.S. Pat. No. 5,631,359; an example of the hepatitis delta virus motif is described by Perrotta and Been, 1992 *Biochemistry* 31, 16; Been et al., U.S. Pat. No. 5,625,047; of the RNaseP motif by Guerrier-Takada et al., 1983 *Cell* 35, 849; Forster and Altman, 1990 *Science* 249, 783; *Neurospora* VS RNA ribozyme motif is described by Collins (Saville and Collins, 1990 *Cell* 61, 685–696; Saville and Collins, 1991 *Proc. Natl. Acad. Sci. USA* 88, 8826–8830; Guo and Collins, 1995 *EMBO J.* 14, 368) and of the Group I intron by Zaug et al., 1986, Nature, 324, 429; Cech et al., U.S. Pat. No. 4,987,071. (All these publications are hereby incorporated by references herein.) These specific motifs are not limiting in the invention and those skilled in the art will recognize that all that is important in an enzymatic nucleic acid molecule with endonuclease activity of this invention is that it has a specific substrate binding site which is complementary to one or more of the target gene RNA and that it have nucleotide sequences within or surrounding that substrate binding site which impart an RNA cleaving activity to the molecule. The length of the binding site varies for different ribozyme motifs, and a person skilled in the art will recognize that to achieve an optimal ribozyme activity the length of the binding arm should be of sufficient length to form a stable interaction with the target nucleic acid sequence.

Catalytic activity of the ribozymes described in the instant invention can be optimized as described by Draper et al., supra. The details will not be repeated here, but include altering the length of the ribozyme binding arms, or chemically synthesizing ribozymes with modifications (base, sugar and/or phosphate) that prevent their degradation by serum ribonucleases and/or enhance their enzymatic activity (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of enzymatic RNA molecules). Modifications which enhance their efficacy in cells, and removal of bases from stem loop structures to shorten RNA synthesis times and reduce chemical requirements are desired. (All these publications are hereby incorporated by reference herein).

There are several examples in the art describing sugar and phosphate modifications that can be introduced into enzymatic nucleic acid molecules without significantly effecting catalysis and with significant enhancement in their nuclease stability and efficacy. Ribozymes are modified to enhance stability and/or enhance catalytic activity by modification with nuclease resistant groups, for example, 2'-amino, 2'-C-allyl, 2'-flouro, 2'-O-methyl, 2'-H, nucleotide base modifications (for a review see Usman and Cedergren, 1992 *TIBS* 17, 34; Usman et al., 1994 *Nucleic Acids Symp. Ser.* 31, 163; Burgin et al., 1996 *Biochemistry* 35, 14090). Sugar modification of enzymatic nucleic acid molecules have been extensively described in the art (see Eckstein et al., *International Publication* PCT No. WO 92/07065; Perrault et al. *Nature* 1990, 344, 565–568; Pieken et al. *Science* 1991, 253, 314–317; Usman and Cedergren, *Trends in Biochem. Sci.* 1992, 17, 334–339; Usman et al. *International Publication* PCT No. WO 93/15187; Sproat, U.S. Pat. No. 5,334,711 and Beigelman et al., 1995 *J. Biol. Chem.* 270, 25702; all of the references are hereby incorporated in their totality by reference herein).

Such publications describe general methods and strategies to determine the location of incorporation of sugar, base and/or phosphate modifications and the like into ribozymes without inhibiting catalysis, and are incorporated by reference herein. In view of such teachings, similar modifications can be used as described herein to modify the nucleic acid catalysts of the instant invention.

Nucleic acid catalysts having chemical modifications which maintain or enhance enzymatic activity are provided. Such nucleic acid is also generally more resistant to nucleases than unmodified nucleic acid. Thus, in a cell and/or in vivo the activity may not be significantly lowered. As exemplified herein such ribozymes are useful in a cell and/or in vivo even if activity over all is reduced 10 fold (Burgin et al., 1996, *Biochemistry,* 35, 14090). Such ribozymes herein are said to "maintain" the enzymatic activity on all RNA ribozyme.

Therapeutic ribozymes delivered exogenously must optimally be stable within cells until translation of the target RNA has been inhibited long enough to reduce the levels of the undesirable protein. This period of time varies between hours to days depending upon the disease state. Clearly, ribozymes must be resistant to nucleases in order to function as effective intracellular therapeutic agents. Improvements in the chemical synthesis of RNA (Wincott et al., 1995 *Nucleic Acids Res.* 23, 2677; incorporated by reference herein) have expanded the ability to modify ribozymes by introducing nucleotide modifications to enhance their nuclease stability as described above.

By "nucleotide" as used herein is as recognized in the art to include natural bases (standard), and modified bases well known in the art. Such bases are generally located at the 1' position of a sugar moiety. Nucleotide generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; all hereby incorporated by reference herein). There are several examples of modified nucleic acid bases known in the art and has recently been summarized by Limbach et al., 1994, *Nucleic Acids Res.* 22, 2183. Some of the non-limiting examples of base modifications that can be introduced into enzymatic nucleic acids without significantly effecting their catalytic activity include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g. ribothymidine), 5-halouridine (e.g., 5-bromouridine) or 6-azapyrimidines or 6-alkylpyrimidines (e.g. 6-methyluridine) and others (Burgin et al., 1996, *Biochemistry,* 35, 14090). By "modified bases" in this aspect is meant nucleotide bases other than adenine, guanine, cytosine and uracil at 1' position or their equivalents; such bases may be used within the catalytic core of the enzyme and/or in the substrate-binding regions.

By "unmodified nucleoside" is meant one of the bases adenine, cytosine, guanine, uracil joined to the 1' carbon of b-D-ribo-furanose.

By "modified nucleoside" is meant any nucleotide base which contains a modification in the chemical structure of an unmodified nucleotide base, sugar and/or phosphate.

Various modifications to ribozyme structure can be made to enhance the utility of ribozymes. Such modifications will enhance shelf-life, half-life in vitro, stability, and ease of introduction of such ribozymes to the target site, eg., to enhance penetration of cellular membranes, and confer the ability to recognize and bind to targeted cells.

Administration of Polynucleotides

Sullivan et al., PCT WO 94/02595, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., PCT WO93/23569 which have been incorporated by reference herein.

The molecules of the instant invention can be used as pharmaceutical agents. Pharmaceutical agents prevent, inhibit the occurrence, or treat (alleviate a symptom to some extent, preferably all of the symptoms) of a disease state in a patient.

By "patient" is meant an organism which is a donor or recipient of explanted cells or the cells themselves. "Patient" also refers to an organism to which the compounds of the invention can be administered. Preferably, a patient is a mammal, e.g., a human, primate or a rodent.

The negatively charged polynucleotides of the invention can be administered (e.g., RNA, DNA or protein) and introduced into a patient by any standard means, with or without stabilizers, buffers, and the like, to form a pharmaceutical composition. When it is desired to use a liposome delivery mechanism, standard protocols for formation of liposomes can be followed. The compositions of the present invention may also be formulated and used as tablets, capsules or elixirs for oral administration; suppositories for rectal administration; sterile solutions; suspensions for injectable administration; and the like.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or patient, preferably a human. Suitable forms, in part, depend upon the use or the route of entry, for example oral, transdermal, or by injection. Such forms should not prevent the composition or formulation to reach a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

By "systemic administration" is meant in vivo systemic absorption or accumulation of drugs in the blood stream followed by distribution throughout the entire body. Administration routes which lead to systemic absorption include, without limitations: intravenous, subcutaneous, intraperitoneal, inhalation, oral, intrapulmonary and intramuscular. Each of these administration routes expose the desired negatively charged polymers, e.g., nucleic acids, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful. This approach may provide enhanced delivery of the drug to target cells by taking advantage of the specificity of macrophage and lymphocyte immune recognition of abnormal cells, such as the cancer cells.

The invention also features the use of the a composition comprising surface-modified liposomes containing poly (ethylene glycol) lipids (PEG-modified, or long-circulating liposomes or stealth liposomes). These formulations offer an method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601–2627; Ishiwataet al., *Chem. Pharm. Bull.* 1995, 43, 1005–1011). Such liposomes have been shown to accumulate selectively in tumors, presumably by extravasation and capture in the neovascularized target tissues (Lasic et al., *Science* 1995, 267, 1275–1276; Oku et al., 1995, *Biochim. Biophys. Acta,* 1238, 86–90). The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 1995, 42, 24864–24870; Choi et al., International PCT Publication No. WO 96/10391; Ansell et al., International PCT Publication No. WO 96/10390; Holland et al., International PCT Publication No. WO 96/10392; all of these are incorporated by reference herein). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences,* Mack Publishing Co. (A. R. Gennaro edit. 1985) hereby incorporated by reference herein. For example, preservatives, stabilizers, dyes and flavoring agents may be provided. Id. at 1449. These include sodium benzoate, sorbic acid and esters of p-hydroxybenzoic acid. In addition, antioxidants and suspending agents may be used. Id.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered dependent upon potency of the negatively charged polymer.

EXAMPLES

The following are non-limiting examples showing the synthesis and activity of the certain compounds of Formula I of the instant invention and polynucleotides comprising one or more of these compounds. Those in the art will recognize that certain reaction conditions such as temperatures, pH, ionic conditions, reaction times and solvent conditions described in the following examples are not meant to be limiting and can be readily modified without significantly effecting the synthesis.

Example 1

Synthesis of Xylo Nucleoside Phosphoramidite
Preparation of Protected 1-(β-D-xylopentofuranosyl) nucleoside Referring to FIG. 2, 2'-O-TBDMS-5'-O-DMT ribonucleoside 1 (2 mmol) was added to a solution of $CrO_3$ (600 mg), pyridine (1 ml) and acetic anhydride (0.6 ml) in $CH_2Cl_2$ (15 ml) and the reaction mixture stirred at room temperature for 1 hour. Ethyl acetate (100 ml) was then added and the mixture filtered through a Celite pad. The filtrate was concentrated in vacuo (40° C.), ethyl acetate (100 ml) was added and the mixture filtered slowly through the mixture of silica gel and Florisil (1:1, 40 g). The filtrate was concentrated in vacuo (40° C.) and used directly in the next step.

The above material was dissolved in ethanol (30 ml) and $NaB(OAc)_3H$ (848 mg, 2 eq) was added. The reaction mixture was stirred at room temperature overnight and the solvent removed in vacuo. The residue was partitioned between ethyl acetate and brine, organic layer was washed with aqueous 5% $NaHCO_3$ solution, dried ($Na_2SO_4$) and evaporated to a colorless foam. Purification by flash silica gel column chromatography using $CH_2Cl_2$/MeOH or $CH_2CH_2Cl_2$/THF mixtures yielded pure products (scheme 1, 2) in 60–75% yield (based on the starting ribo nucleosides).
Preparation of 3'-O-phosphoramidites 3'-O-Phosphoramidites 3 were prepared in 65–70(G) or-75–85(A) % yield using the standard phosphitylation procedure (Tuschl, T., et al. *Biochemistry* 1993, 32, 11658–11668).

This scheme can be used to synthesize xylo nucleoside phosphoramidites such as xyloadenosine, xyloguanosine, xylouridine, xylocytidine and others.

Example 2

Incorporation of Phosphoramidites into Ribozymes

The above monomers 3 were incorporated into ribozymes using standard procedures (Wincott, et al. *Nucleic Acids Res* 1995, 23, 2677–2684; Usman et al., *J. Am. Chem. Soc.* 1987, 109, 7845–7854; Scaringe et al., *Nucleic Acids Res.* 1990, 18, 5433–5441) and makes use of common nucleic acid protecting and coupling groups, such as dimethoxytrityl at the 5'-end, and phosphoramidites at the 3'-end. The average stepwise coupling yields were >98%. These nucleotides may be incorporated not only into hammerhead ribozymes, but also into hairpin, VS ribozymes, hepatitis delta virus, or Group I or Group II introns. They are, therefore, of general use as replacement motifs in any nucleic acid structure. The coupling time for the incorporation of modified phosphoramidites was extended to 20 minutes (Seela, F., et al. 1 *Helv. Chim. Acta* 1994, 77, 883–895). Examples of ribozyme synthesized according to this invention are shown in FIG. 3.

Example 3

Cleavage of Short Substrate Using Xylo Modified Ribozymes

Ribozyme Reactions:

Ribozyme (1 μM) was incubated in 50 mM Tris (pH 8.0) and 10 mM $MgCl_2$ at 37° C. with trace amounts of short substrate (>1 nMol of RNA). Reaction times were modulated to give accurate kinetics of cleavage values. Ribozyme with xylo A residue at A15.1 and/or A6 demonstrated the same cleavage activity as parent "5-Ribo" motif (Table IIIA). Incorporation of xylo G at G12 is also tolerated though cleavage activity is reduced by 5 fold (Table IIIB).
Diagnostic Uses Ribozymes of this invention may be used as diagnostic tools to examine genetic drift and mutations within diseased cells or to detect the presence of a specific RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Additional Uses

Nucleic acid molecules of the instant invention might have many of the same applications for the study of RNA that DNA restriction endonucleases have for the study of DNA (Nathans et al., 1975 *Ann. Rev. Biochem.* 44:273). For example, the pattern of restriction fragments could be used to establish sequence relationships between two related RNAs, and large RNAs could be specifically cleaved to fragments of a size more useful for study. The ability to engineer sequence specificity of the ribozyme is ideal for cleavage of RNAs of unknown sequence. Nucleic acid molecules (e.g., ribozymes) of the invention can be used, for example, to target cleavage of virtually any RNA transcript (Zaug et al., 324, *Nature* 429 1986; Cech, 260 *JAMA* 3030, 1988; and Jefferies et al., 17 *Nucleic Acids Research* 1371, 1989). Such nucleic acids can be used as a therapeutic or to validate a therapeutic gene target and/or to determine the function of a gene in a biological system (Christoffersen, 1997, *Nature Biotech.* 15, 483).

Various ligands can be attached to oligonucleotides using the componds of Formula I for the purposes of cellular delivery, nuclease resistance, cellular trafficking and localization, chemical ligation of oligonucleotide fragments.

Incorporation of one or more compounds of Formula I into a ribozyme may increase its effectiveness. Compounds of Formula I can be used as potential antiviral agents.

Other embodiments are within the following claims.

TABLE I

Characteristics of naturally occurring ribozymes

Group I Introns

Size: ~150 to >1000 nucleotides.
Requires a U in the target sequence immediately 5' of the cleavage site.
Binds 4–6 nucleotides at the 5'-side of the cleavage site.
Reaction mechanism: attack by the 3'-OH of guanosine to generate cleavage products with 3'-OH and 5'-guanosine.
Additional protein cofactors required in some cases to help folding and maintainance of the active structure.
Over 300 known members of this class. Found as an intervening sequence in *Tetrahymena thermophila* rRNA, fungal mitochondria, chloroplasts, phage T4, blue-green algae, and others.
Major structural features largely established through phylogenetic comparisons, mutagenesis, and biochemical studies [i,ii]
Complete kinetic framework established for one ribozyme [iii,iv,v,vi].
Studies of ribozyme folding and substrate docking underway [vii,viii,ix].
Chemical modification investigation of important residues well established [x,xi].
The small (4–6 nt) binding site may make this ribozyme too non-specific for targeted RNA cleavage, however, the Tetrahymena group I intron has been used to repair a "defective" β-galactosidase message by the ligation of new β-galactosidase sequences onto the defective message [xii].

RNAse P RNA (M1 RNA)

Size: ~290 to 400 nucleotides.
RNA portion of a ubiquitous ribonucleoprotein enzyme.
Cleaves tRNA precursors to form mature tRNA [xiii].
Reaction mechanism: possible attack by $M^{2+}$-OH to generate cleavage products with 3'-OH and 5'-phosphate.
RNAse P is found throughout the prokaryotes and eukaryotes. The RNA subunit has been sequenced from bacteria, yeast, rodents, and primates.
Recruitment of endogenous RNAse P for therapeutic applications is possible through hybridization of an External Guide Sequence (EGS) to the target RNA [xiv,xv]
Important phosphate and 2' OH contacts recently identified [xvi,xvii]

Group II Introns

Size: >1000 nucleotides.
Trans cleavage of target RNAs recently demonstrated [xviii,xix].
Sequence requirements not fully determined.
Reaction mechanism: 2'-OH of an internal adenosine generates cleavage products with 3'-OH and a "lariat" RNA containing a 3'-5' and a 2'-5' branch point.
Only natural ribozyme with demonstrated participation in DNA cleavage [xx,xxi] in addition to RNA cleavage and ligation.
Major structural features largely established through phylogenetic comparisons [xxii].
Important 2' OH contacts beginning to be identified [xxiii]
Kinetic framework under development [xxiv]

Neurospora VS RNA

Size: ~144 nucleotides.
Trans cleavage of hairpin target RNAs recently demonstrated [xxv].
Sequence requirements not fully determined.
Reaction mechanism: attack by 2'-OH 5' to the scissile bond to generate cleavage products with 2',3'-cyclic phosphate and 5'-OH ends.
Binding sites and structural requirements not fully determined.
Only 1 known member of this class. Found in Neurospora VS RNA.

Hammerhead Ribozyme
(see text for references)

Size: ~13 to 40 nucleotides.
Requires the target sequence UH immediately 5' of the cleavage site.
Binds a variable number nucleotides on both sides of the cleavage site.
Reaction mechanism: attack by 2'-OH 5' to the scissile bond to generate cleavage products with 2',3'-cyclic phosphate and 5'-OH ends.
14 known members of this class. Found in a number of plant pathogens (virusoids) that use RNA as the infectious agent.
Essential structural features largely defined, including 2 crystal structures [xxvi,xxvii]
Minimal ligation activity demonstrated (for engineering through in vitro selection) [xxviii]

TABLE I-continued

Characteristics of naturally occurring ribozymes

Complete kinetic framework established for two or more ribozymes [xxix].
Chemical modification investigation of important residues well established [xxx].

Hairpin Ribozyme

Size: ~50 nucleotides.
Requires the target sequence GUC immediately 3' of the cleavage site.
Binds 4–6 nucleotides at the 5'-side of the cleavage site and a variable number to the 3'-side of the cleavage site.
Reaction mechanism: attack by 2'-OH 5' to the scissile bond to generate cleavage products with 2',3'-cyclic phosphate and 5'-OH ends.
3 known members of this class. Found in three plant pathogen (satellite RNAs of the tobacco ringspot virus, arabis mosaic virus and chicory yellow mottle virus) which uses RNA as the infectious agent.
Essential structural features largely defined [xxxi,xxxii,xxxiii,xxxiv]
Ligation activity (in addition to cleavage activity) makes ribozyme amenable to engineering through in vitro selection [xxxv]
Complete kinetic framework established for one ribozyme [xxxvi].
Chemical modification investigation of important residues begun [xxxvii,xxxviii].

Hepatitis Delta Virus (HDV) Ribozyme

Size: ~60 nucleotides.
Trans cleavage of target RNAs demonstrated [xxxix].
Binding sites and structural requirements not fully determined, although no sequences 5' of cleavage site are required. Folded ribozyme contains a pseudoknot structure [xl].
Reaction mechanism: attack by 2'-OH 5' to the scissile bond to generate cleavage products with 2',3'-cyclic phosphate and 5'-OH ends.
Only 2 known members of this class. Found in human HDV.
Circular form of HDV is active and shows increased nuclease stability [xli]

[i]. Michel, Francois; Westhof, Eric. Slippery substrates. Nat. Struct. Biol. (1994), 1(1), 5–7.
[ii]. Lisacek, Frederique; Diaz, Yolande; Michel, Francois. Automatic identification of group I intron cores in genomic DNA sequences. J. Mol. Biol. (1994), 235(4), 1206–17.
[iii]. Herschlag, Daniel; Cech, Thomas R.. Catalysis of RNA cleavage by the Tetrahymena thermophila ribozyme. 1. Kinetic description of the reaction of an RNA substrate complementary to the active site. Biochemistry (1990), 29(44), 10159–71.
[iv]. Herschlag, Daniel; Cech, Thomas R.. Catalysis of RNA cleavage by the Tetrahymena thermophila ribozyme. 2. Kinetic description of the reaction of an RNA substrate that forms a mismatch at the active site. Biochemistry (1990), 29(44), 10172–80.
[v]. Knitt, Deborah S.; Herschlag, Daniel. pH Dependencies of the Tetrahymena Ribozyme Reveal an Unconventional Origin of an Apparent pKa. Biochemistry (1996), 35(5), 1560–70.
[vi]. Bevilacqua, Philip C.; Sugimoto, Naoki; Turner, Douglas H.. A mechanistic framework for the second step of splicing catalyzed by the Tetrahymena ribozyme. Biochemistry (1996), 35(2), 648–58.
[vii]. Li, Yi; Bevilacqua, Philip C.; Mathews, David; Turner, Douglas H.. Thermodynamic and activation parameters for binding of a pyrene-labeled substrate by the Tetrahymena ribozyme: docking is not diffusion-controlled and is driven by a favorable entropy change. Biochemistry (1995), 34(44), 14394–9.
[viii]. Banerjee, Aloke Raj; Turner, Douglas H.. The time dependence of chemical modification reveals slow steps in the folding of a group I ribozyme. Biochemistry (1995), 34(19), 6504–12.
[ix]. Zarrinkar, Patrick P.; Williamson, James R.. The P9.1–P9.2 peripheral extension helps guide folding of the Tetrahymena ribozyme. Nucleic Acids Res. (1996), 24(5), 854–8.
[x]. Strobel, Scott A.; Cech, Thomas R.. Minor groove recognition of the conserved G.cntdot.U pair at the Tetrahymena ribozyme reaction site. Science (Washington, D.C.) (1995), 267(5198), 675–9.
[xi]. Strobel, Scott A.; Cech, Thomas R.. Exocyclic Amine of the Conserved G.cntdot.U Pair at the Cleavage Site of the Tetrahymena Ribozyme Contributes to 5'-Splice Site Selection and Transition State Stabilization. Biochemistry (1996), 35(4), 1201–11.
[xii]. Sullenger, Bruce A.; Cech, Thomas R.. Ribozyme-mediated repair of defective mRNA by targeted trans-splicing. Nature (London) (1994), 371 (6498), 619–22.
[xiii]. Robertson, H. D.; Altman, S.; Smith, J. D. J. Biol. Chem., 247, 5243–5251 (1972).
[xiv]. Forster, Anthony C.; Altman, Sidney. External guide sequences for an RNA enzyme. Science (Washington, D.C., 1883-) (1990), 249(4970), 783–6.
[xv]. Yuan, Y.; Hwang, E. S.; Altman, S. Targeted cleavage of mRNA by human RNase P. Proc. Natl. Acad. Sci. USA (1992) 89, 8006–10.

[xvi]. Harris, Michael E.; Pace, Norman R.. Identification of phosphates involved in catalysis by the ribozyme RNase P RNA. RNA (1995), 1(2), 210–18.
[xvii]. Pan, Tao; Lana, Andrew; Zhong, Kun. Probing of tertiary interactions in RNA: 2'-hydroxyl-base contacts between the RNase P RNA and pre-tRNA. Proc. Natl. Acad. Sci. U.S.A. (1995), 92(26), 12510–14.
[xviii]. Pyle, Anna Marie; Green, Justin B.. Building a Kinetic Framework for Group II Intron Ribozyme Activity: Quantitation of Interdomain Binding and Reaction Rate. Biochemistry (1994), 33(9), 2716–25.
[xix]. Michels, William J. Jr.; Pyle, Anna Marie. Conversion of a Group II Intron into a New Multiple-Turnover Ribozyme that Selectively Cleaves Oligonucleotides: Elucidation of Reaction Mechanism and Structure/Function Relationships. Biochemistry (1995), 34(9), 2965–77.
[xx]. Zimmerly, Steven; Guo, Huatao; Eskes, Robert; Yang, Jian; Perlman, Philip S.; Lambowitz, Alan M.. A group II intron RNA is a catalytic component of a DNA endonuclease involved in intron mobility. Cell (Cambridge, Mass.) (1995), 83(4), 529–38.
[xxi]. Griffin, Edmund A., Jr.; Qin, Zhifeng; Michels, Williams J., Jr.; Pyle, Anna Marie. Group II intron ribozymes that cleave DNA and RNA linkages with similar efficiency, and lack contacts with substrate 2'-hydroxyl groups. Chem. Biol. (1995), 2(11), 761–70.
[xxii]. Michel, Francois; Ferat, Jean Luc. Structure and activities of group II introns. Annu. Rev. Biochem. (1995), 64, 435–61.
[xxiii]. Abramovitz, Dana L.; Friedman, Richard A.; Pyle, Anna Marie. Catalytic role of 2'-hydroxyl groups within a group II intron active site. Science (Washington, D.C.) (1996), 271(5254), 1410–13.
[xxiv]. Daniels, Danette L.; Michels, William J., Jr.; Pyle, Anna Marie. Two competing pathways for self-splicing by group II introns: a quantitative analysis of in vitro reaction rates and products. J. Mol. Biol. (1996), 256 (1), 31–49.
[xxv]. Guo, Hans C. T.; Collins, Richard A.. Efficient trans-cleavage of a stem-loop RNA substrate by a ribozyme derived from Neurospora VS RNA. EMBO J. (1995), 14(2), 368–76.
[xxvi]. Scott, W. G., Finch, J. T., Aaron, K. The crystal structure of an all RNA hammerhead ribozyme:Aproposed mechanism for RNA catalytic cleavage. Cell, (1995), 81, 991–1002.
[xxvii]. McKay, Structure and function of the hammerhead ribozyme: an unfinished story. RNA, (1996), 2, 395–403.
[xxviii]. Long, D., Uhlenbeck, O., Hertel, K. Ligation with hammerhead ribozymes. U.S. Pat. No. 5,633,133.
[xxix]. Hertel, K. J., Herschlag, D., Uhlenbeck, O. A kinetic and thermodynamic framework for the hammerhead ribozyme reaction. Biochemistry, (1994) 33, 3374–3385. Beigelman, L., et al., Chemical modifications of hammerhead ribozymes. J. Biol. Chem., (1995) 270, 25702–25708.
[xxx]. Beigelman, L., et al., Chemical modifications of hammerhead ribozymes. J. Biol. Chem., (1995) 270, 25702–25708.
[xxxi]. Hampel, Arnold; Tritz, Richard; Hicks, Margaret; Cruz, Phillip. 'Hairpin' catalytic RNA model: evidence for helixes and sequence requirement for substrate RNA. Nucleic Acids Res. (1990), 18(2), 299–304.
[xxxii]. Chowrira, Bharat M.; Berzal-Herranz, Alfredo; Burke, John M.. Novel guanosine requirement for catalysis by the hairpin ribozyme. Nature (London) (1991), 354(6351), 320–2.
[xxxiii]. Berzal-Herranz, Alfredo; Joseph, Simpson; Chowrira, Bharat M.; Butcher, Samuel E.; Burke, John M.. Essential nucleotide sequences and secondary structure elements of the hairpin ribozyme. EMBO J. (1993), 12(6), 2567–73.
[xxxiv]. Joseph, Simpson; Berzal-Herranz, Alfredo; Chowrira, Bharat M.; Butcher, Samuel E.. Substrate selection rules for the hairpin ribozyme determined by in vitro selection, mutation, and analysis of mismatched substrates. Genes Dev. (1993), 7(1), 130–8.
[xxxv]. Berzal-Herranz, Alfredo; Joseph, Simpson; Burke, John M.. In vitro selection of active hairpin ribozymes by sequential RNA-catalyzed cleavage and ligation reactions. Genes Dev. (1992), 6(1), 129–34.
[xxxvi]. Hegg, Lisa A.; Fedor, Martha J.. Kinetics and Thermodynamics of Intermolecular Catalysis by Hairpin Ribozymes. Biochemistry (1995), 34(48), 15813–28.
[xxxvii]. Grasby, Jane A.; Mersmann, Karin; Singh, Mohinder; Gait, Michael J.. Purine Functional Groups in Essential Residues of the Hairpin Ribozyme Required for Catalytic Cleavage of RNA. Biochemistry (1995), 34(12). 4068–76.
[xxxviii]. Schmidt, Sabine; Beigelman, Leonid; Karpeisky, Alexander; Usman, Nassim; Sorensen, Ulrik S.; Gait, Michael J.. Base and sugar requirements for RNA cleavage of essential nucleoside residues in internal loop B of the hairpin ribozyme: implications for secondary structure. Nucleic Acids Res. (1996), 24(4), 573–81.
[xxxix]. Perrotta, Anne T.; Been, Michael D.. Cleavage of oligoribonucleotides by a ribozyme derived from the hepatitis .delta. virus RNA sequence. Biochemistry (1992), 31(1), 16–21.

TABLE I-continued

Characteristics of naturally occurring ribozymes xl. Perrotta, Anne T.; Been, Michael D.. A pseudoknot-like structure required for efficient self-cleavage of hepatitis delta virus RNA. Nature (London) (1991), 350(6317), 434–6.
xlii. Puttaraju, M.; Perrotta, Anne T.; Been, Michael D.. A circular trans-acting hepatitis delta virus ribozyme. Nucleic Acids Res. (1993), 21(18), 4253–8.

TABLE II 2.5 μmol RNA Synthesis Cycle

| Reagent | Equivalents | Amount | Wait Time* |
|---|---|---|---|
| Phosphoramidites | 6.5 | 163 μL | 2.5 |
| S-Ethyl Tetrazole | 23.8 | 238 μL | 2.5 |
| Acetic Anhydride | 100 | 233 μL | 5 sec |
| N-Methyl Imidazole | 186 | 233 μL | 5 sec |
| TCA | 83.2 | 1.73 mL | 21 sec |
| Iodine | 8.0 | 1.18 mL | 45 sec |
| Acetonitrile | NA | 6.67 mL | NA |

*Wait time does not include contact time during delivery.

TABLE IIIA

| Ribozyme | $K_{obs}$ (min$^{-1}$) | $K_{rel}$ |
|---|---|---|
| A | 4 | 1 |
| B | 0.7 | 0.2 |
| C | 0.002 | 0.0005 |
| D | 0.004 | 0.001 |

TABLE IIIB

| Ribozyme | $K_{obs}$ (min$^{-1}$) | $K_{rel}$ |
|---|---|---|
| A | 0.32938 | 1.00 |
| E | 0.29395 | 0.89 |
| F | 0.22249 | 0.68 |
| G | 0.28201 | 0.86 |

A - all RNA 36mer Hammerhead Ribozyme

What is claimed is:

1. A polynucleotide comprising a compound of the following formula at one or more positions:

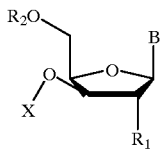

wherein
R$_1$ is —OH, —O—R$_3$, —C—R$_3$, halo, —NHR$_4$, —ONHR$_5$ or —ON=R$_6$;
R$_2$ is independently blocking group or a phosphorus-containing group;
B is independently a nucleotide base or its analog or hydrogen;
X is independently a phosphorus-containing group;
R$_3$ is independently a moiety selected from a group consisting of alkyl, alkenyl, alkynyl, aryl, alkylaryl, carbocyclic aryl, heterocyclic aryl, amide and ester;
R$_4$ is independently a moiety selected from a group consisting of alkyl (C1–22), acyl (C1–22), substituted or unsubstituted aryl, or —OCH$_2$SCH$_3$ (methylthiomethyl);
R$_5$ is independently a moiety selected from a group consisting of H, aminoacyl group, peptidyl group, biotinyl group, cholesteryl group, lipoic acid residue, retinoic acid residue, folic acid residue, ascorbic acid residue, nicotinic acid residue, 6-aminopenicillanic acid residue, 7-aminocephalosporanic acid residue, alkyl, alkenyl, alkynyl, aryl, alkylaryl, carbocyclic aryl, heterocyclic aryl, amide or ester; and
R$_6$ is independently pyridoxal residue, pyridoxal-5-phosphate residue, 13-cis-retinal residue, 9-cis-retinal residue, alkyl, alkenyl, alkynyl, alkylaryl, carbocyclic alkylaryl, or heterocyclic alkylaryl;
the polynucleotide having one or more 2'-hydroxylamino moieties.

2. The polynucleotide of claim 1, wherein said polynucleotide is an enzymatic nucleic acid.

3. The enzymatic nucleic acid of claim 2, wherein said nucleic acid is in a hammerhead configuration.

4. The enzymatic nucleic acid of claim 2, wherein said nucleic acid is in a hairpin configuration.

5. The enzymatic nucleic acid of claim 2, wherein said nucleic acid is in a hepatitis delta virus, group I intron, VS RNA, group II intron or RNase P RNA configuration.

6. A pharmaceutical composition comprising a polynucleotide of claim 2.

7. The polynucleotide of claim 1 wherein the one or more 2'-hydroxylamino moieties reacts with an aldehyde to form an oxime.

8. The polynucleotide of claim 7, wherein said polynucleotide is an enzymatic nucleic acid.

9. The enzymatic nucleic acid of claim 8, wherein said nucleic acid is in a hammerhead configuration.

10. The enzymatic nucleic acid of claim 8, wherein said nucleic acid is in a hairpin configuration.

11. The enzymatic nucleic acid of claim 8, wherein said nucleic acid is in a hepatitis delta virus, group I intron, VS RNA, group II intron or RNase P RNA configuration.

12. A pharmaceutical composition comprising a polynucleotide of claim 8.

13. The polynucleotide of claim 1 wherein the one or more 2'-hydroxylamino moieties reacts with a carboxylic acid to form an oxyamides.

14. The polynucleotide of claim 13, wherein said polynucleotide is an enzymatic nucleic acid.

15. The enzymatic nucleic acid of claim 14, wherein said nucleic acid is in a hammerhead configuration.

16. The enzymatic nucleic acid of claim 14, wherein said nucleic acid is in a hairpin configuration.

17. The enzymatic nucleic acid of claim 14, wherein said nucleic acid is in a hepatitis delta virus, group I intron, VS RNA, group II intron or RNase P RNA configuration.

18. A pharmaceutical composition comprising a polynucleotide of claim 14.

19. A compound of the formula

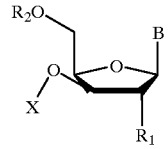

wherein
R$_1$ is —OH, —O—R$_3$, —C—R$_3$, halo, —NHR$_4$, —ONHR$_5$ or —ON=R$_6$;

$R_2$ is independently blocking group or a phosphorus-containing group;

B is independently a nucleotide base or its analog or hydrogen;

X is independently a phosphorus-containing group;

$R_3$ is independently a moiety selected from a group consisting of alkyl, alkenyl, alkynyl, aryl, alkylaryl, carbocyclic aryl, heterocyclic aryl, amide and ester;

$R_4$ is independently a moiety selected from a group consisting of alkyl (C1–22), acyl (C1–22), substituted or unsubstituted aryl, or —OCH$_2$SCH$_3$ (methylthiomethyl);

$R_5$ is independently a moiety selected from a group consisting of H, aminoacyl group, peptidyl group, biotinyl group, cholesteryl group, lipoic acid residue, retinoic acid residue, folic acid residue, ascorbic acid residue, nicotinic acid residue, 6-aminopenicillanic acid residue, 7-aminocephalosporanic acid residue, alkyl, alkenyl, alkynyl, aryl, alkylaryl, carbocyclic aryl, heterocyclic aryl, amide or ester; and $R_6$ is independently pyridoxal residue, pyridoxal-5-phosphate residue, 13-cis-retinal residue, 9-cis-retinal residue, alkyl, alkenyl, alkynyl, alkylaryl, carbocyclic alkylaryl, or heterocyclic alkylaryl;

wherein the compound is used as an anticancer or anti-tumor agent.

20. An enzymatic nucleic acid comprising a compound of the following formula at one or more positions:

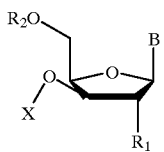

wherein $R_1$ is —OH, —O—$R_3$, —C—$R_3$, halo, —NHR$_4$, —ONHR$_5$ or —ON=R$_6$;

$R_2$ is independently blocking group or a phosphorus-containing group;

B is independently a nucleotide base or its analog or hydrogen;

X is independently a phosphorus-containing group;

$R_3$ is independently a moiety selected from a group consisting of alkyl, alkenyl, alkynyl, aryl, alkylaryl, carbocyclic aryl, heterocyclic aryl, amide and ester;

$R_4$ is independently a moiety selected from a group consisting of alkyl (C1–22), acyl (C1–22), substituted or unsubstituted aryl, or —OCH$_2$SCH$_3$ (methylthiomethyl);

$R_5$ is independently a moiety selected from a group consisting of H, aminoacyl group, peptidyl group, biotinyl group, cholesteryl group, lipoic acid residue, retinoic acid residue, folic acid residue, ascorbic acid residue, nicotinic acid residue, 6-aminopenicillanic acid residue, 7-aminocephalosporanic acid residue, alkyl, alkenyl, alkynyl, aryl, alkylaryl, carbocyclic aryl, heterocyclic aryl, amide or ester; and $R_6$ is independently pyridoxal residue, pyridoxal-5-phosphate residue, 13-cis-retinal residue, 9-cis-retinal residue, alkyl, alkenyl, alkynyl, alkylaryl, carbocyclic alkylaryl, or heterocyclic alkylaryl;

the enzymatic nucleic acid having complimentarity with a target nucleic acid molecule.

* * * * *